United States Patent
Zheng et al.

(10) Patent No.: US 9,384,546 B2
(45) Date of Patent: Jul. 5, 2016

(54) METHOD AND SYSTEM FOR PERICARDIUM BASED MODEL FUSION OF PRE-OPERATIVE AND INTRA-OPERATIVE IMAGE DATA FOR CARDIAC INTERVENTIONS

(71) Applicants: Reinhard Boese, Wuerzburg (DE) Ursula Boese, Wuerzburg (DE) Antje Schulte, Eckental (DE)

(72) Inventors: Yefeng Zheng, Dayton, NJ (US); Razvan Ioan Ionasec, Nuremberg (DE); Sasa Grbic, Princeton, NJ (US); Matthias John, Nuremberg (DE); Jan Boese, Eckental (DE); Dorin Comaniciu, Princeton Junction, NJ (US)

(73) Assignee: Siemens Aktiengesellschaft, Munich (DE)

(*) Notice: Subject to any disclaimer, the term of this patent is extended or adjusted under 35 U.S.C. 154(b) by 208 days.

(21) Appl. No.: 13/765,712

(22) Filed: Feb. 13, 2013

(65) Prior Publication Data
US 2013/0294667 A1 Nov. 7, 2013

Related U.S. Application Data

(60) Provisional application No. 61/601,615, filed on Feb. 22, 2012.

(51) Int. Cl.
*G06K 9/00* (2006.01)
*G06T 7/00* (2006.01)
(Continued)

(52) U.S. Cl.
CPC .............. *G06T 7/0012* (2013.01); *A61B 6/503* (2013.01); *A61B 6/5235* (2013.01); *G06K 9/6247* (2013.01); *G06T 7/0024* (2013.01); *A61B 6/12* (2013.01); *A61B 6/4441* (2013.01); *G06T 2207/10081* (2013.01); *G06T 2207/30048* (2013.01); *G06T 2207/30101* (2013.01)

(58) Field of Classification Search
None
See application file for complete search history.

(56) References Cited

U.S. PATENT DOCUMENTS 5,690,106 A * 11/1997 Bani-Hashemi et al. ...... 600/425
5,947,899 A * 9/1999 Winslow .................. A61B 5/00
128/920

(Continued)

OTHER PUBLICATIONS

Rapid Image Registration of Three-Dimensional Transesophageal Echocardiography and X-ray Fluoroscopy for the Guidance of Cardiac Interventions by G. Gao et al. Lecture Notes in Computer Science. vol. 6135. pp. 124-134. 2010.*

(Continued)

*Primary Examiner* — Nancy Bitar

(57) ABSTRACT

A method and system for model based fusion pre-operative image data, such as computed tomography (CT), and intra-operative C-arm CT is disclosed. A first pericardium model is segmented in the pre-operative image data and a second pericardium model is segmented in a C-arm CT volume. A deformation field is estimated between the first pericardium model and the second pericardium model. A model of a target cardiac structure, such as a heart chamber model or an aorta model, extracted from the pre-operative image data is fused with the C-arm CT volume based on the estimated deformation field between the first pericardium model and the second pericardium model. An intelligent weighted average may be used improve the model based fusion results using models of the target cardiac structure extracted from pre-operative image data of patients other than a current patient.

32 Claims, 10 Drawing Sheets (a)

(b)

(51) Int. Cl.
*A61B 6/00* (2006.01)
*G06K 9/62* (2006.01)
*A61B 6/12* (2006.01)

(56) References Cited

U.S. PATENT DOCUMENTS

| | | | |
|---|---|---|---|
| 6,368,285 B1* | 4/2002 | Osadchy et al. | 600/508 |
| 7,010,080 B2 | 3/2006 | Mitshke | |
| 7,117,026 B2 | 10/2006 | Shao et al. | |
| 7,517,318 B2* | 4/2009 | Altmann et al. | 600/459 |
| 7,634,123 B2 | 12/2009 | Florin et al. | |
| 7,916,919 B2 | 3/2011 | Zheng et al. | |
| 8,098,918 B2* | 1/2012 | Zheng | G06T 7/0081 382/131 |
| 8,386,188 B2* | 2/2013 | Taylor | A61B 5/02007 382/128 |
| 8,977,018 B2* | 3/2015 | Buelow | G06T 7/0032 382/128 |
| 2006/0002630 A1* | 1/2006 | Fu | G06K 9/32 382/294 |
| 2006/0099194 A1* | 5/2006 | Geng | A01K 67/0275 424/93.21 |
| 2008/0319308 A1* | 12/2008 | Tang | A61B 5/055 600/416 |
| 2010/0067768 A1* | 3/2010 | Ionasec et al. | 382/131 |
| 2010/0070249 A1* | 3/2010 | Ionasec | G06F 19/321 703/2 |
| 2010/0239148 A1 | 9/2010 | Zheng et al. | |
| 2011/0135173 A1 | 6/2011 | Elbaroudi et al. | |
| 2012/0022843 A1* | 1/2012 | Ionasec et al. | 703/9 |
| 2012/0134564 A1* | 5/2012 | Zheng et al. | 382/131 |
| 2012/0230568 A1* | 9/2012 | Grbic et al. | 382/131 |
| 2012/0296202 A1* | 11/2012 | Mountney et al. | 600/424 |
| 2013/0064438 A1* | 3/2013 | Taylor | A61B 5/02007 382/130 |
| 2013/0066618 A1* | 3/2013 | Taylor | A61B 5/02007 703/11 |

OTHER PUBLICATIONS

Y. Zheng, et al., "Fast and Automatic Heart Isolation in 3D CT Volumes: Optimal Shape Initialization", In Proc. Int'l Workshop on Machine Learning in Medical Imaging (In Conjunction with MICCAI), 2010.

\* cited by examiner

US 9,384,546 B2

METHOD AND SYSTEM FOR PERICARDIUM BASED MODEL FUSION OF PRE-OPERATIVE AND INTRA-OPERATIVE IMAGE DATA FOR CARDIAC INTERVENTIONS

This application claims the benefit of U.S. Provisional Application No. 61/601,615, filed Feb. 22, 2012, the disclosure of which is herein incorporated by reference.

BACKGROUND OF THE INVENTION

The present invention relates to fusion of pre-operative image data with intra-operative image data, and more particularly, to cardiac model based fusion of pre-operative computed tomography (CT) data and intra-operative C-arm CT data.

Minimally invasive transcatheter cardiac interventions are adopted rapidly, especially for high-risk patients, to treat a wide range of cardiovascular diseases, including endovascular stenting for coronary stenoses, valve repair and replacement, and cardiac arrhythmia ablation. Pre-operative imaging plays an important role in cardiac interventions for planning, simulation, and intra-operative visual guidance. Various imaging modalities, such as CT, magnetic resonance imaging (MRI), and ultrasound, may be used for different types of interventions. Pre-operative images often provide detailed delineation of cardiac structures (e.g., in CT or MRI) or cardiac motion information (e.g., cine MRI or real-time ultrasound). Accordingly, such pre-operative images are important for planning of the surgical procedure and simulation of the surgical outcome. Overlaying a cardiac model extracted from pre-operative images onto real-time fluoroscopic images provides valuable visual guidance during cardiac intervention surgeries. However, direct fusion of such a 3D model with an intra-operative fluoroscopic image (3D-to-2D registration) is difficult because the images are captured at different times, on different scanning machines, and sometimes from different cardiac phases. The procedure for directed 3D-to-2D fusion typically requires some amount of user interaction, and contrast agent injection is often required to highlight the target anatomy in the fluoroscopic image in order to facilitate the registration. However, due to side effects of contrast agent, such as renal failure, it is desirable to minimize and, if possible, completely avoid the use of contrast agent.

BRIEF SUMMARY OF THE INVENTION

The present invention provides a method and system for anatomical model-based fusion of pre-operative and intra-operative image data. For example, embodiments of the present invention provide a model-based fusion method that uses the pericardium to align pre-operative computed tomography (CT) to intra-operative C-arm CT. The pericardium is segmented in the CT and C-arm CT images, and a deformation field from CT to the C-arm CT is estimated using the segmented pericardium. Embodiments of the present invention further provide a method for intelligent weighted fusion of multiple cardiac models, including a patient-specific model and/or other available models in a pre-collected data set, in order to further improve accuracy of the fusion results.

In one embodiment of the present invention, a first pericardium model is segmented in a first medical image of a patient acquired using a first imaging modality. A second pericardium model is segmented in a second medical image of the patient acquired using a second imaging modality. A deformation field is estimated between the first pericardium model and the second pericardium model. A model of a target cardiac structure extracted from the first medical image is fused with the second medical image based on the estimated deformation field between the first pericardium model and the second pericardium model.

In another embodiment of the present invention, a plurality of target models of a target anatomical structure, each extracted from a corresponding first medical image acquired using a first medical imaging modality, and a plurality of anchor models of an anchor anatomical structure, each extracted from a corresponding first medical image are used to fuse the target anatomical structure from the first medical imaging modality to a second medical imaging modality. Each of the plurality of target models is aligned to a second medical image of a current patient acquired using the second medical imaging modality using a deformation field calculated between a corresponding one of the plurality of anchor models and a model of the anchor anatomical structure segmented in the second medical image, resulting in a plurality of aligned target models. A respective weight is calculated for each of the plurality of aligned target models based on a distance measure between the corresponding one of the plurality of anchor models and the model of the anchor anatomical structure segmented in the second medical image. A fused model of the target anatomical structure in the second medical image is generated as a weighted average of the plurality of aligned target models using the respective weight calculated for each of the plurality of aligned target models.

These and other advantages of the invention will be apparent to those of ordinary skill in the art by reference to the following detailed description and the accompanying drawings.

DETAILED DESCRIPTION

The present invention is directed to a method and system for anatomical model-based fusion of pre-operative and intra-operative image data. Embodiments of the present invention are described herein to give a visual understanding of the model-based fusion method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
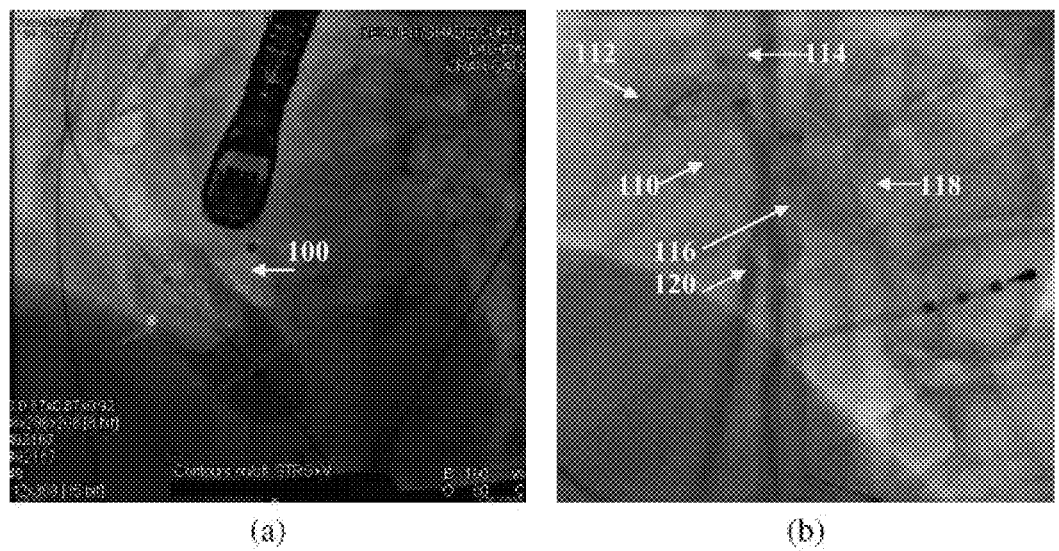
FIG. 1 illustrates exemplary results of overlaying a 3D aorta model and a 3D left atrium model on 2D fluoroscopic images.
Figure 2:
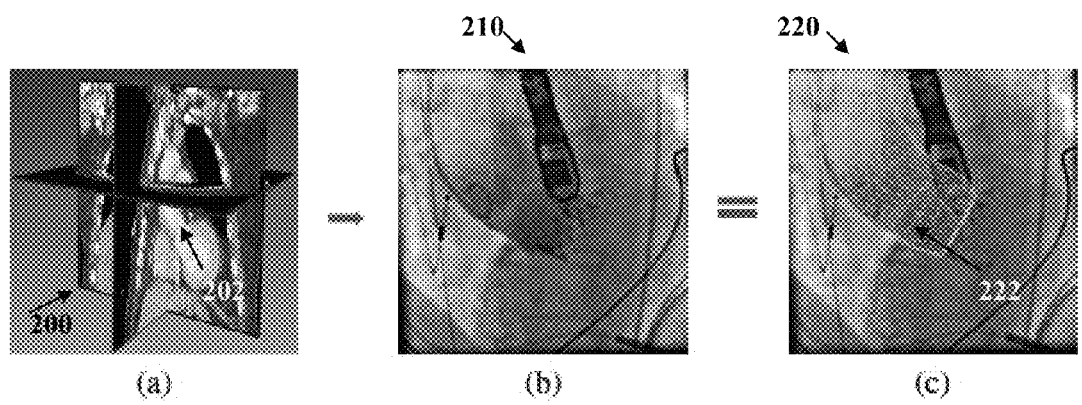
FIG. 2 illustrates a workflow for direct 3D to 2D fusion for a transcatheter aortic valve implantation (TAVI) procedure.

Pre-operative images often provide detailed delineation of cardiac structures (e.g., in CT or MRI) or cardiac motion information (e.g., cine MRI or real-time ultrasound). Accordingly, such pre-operative images are important for planning of the surgical procedure and simulation of the surgical outcome. Overlaying a cardiac model extracted from pre-operative images onto real-time fluoroscopic images provides valuable visual guidance during cardiac intervention surgeries. FIG. 1 illustrates exemplary results of overlaying a 3D aorta model and a 3D left atrium model on 2D fluoroscopic images. Image (a) of FIG. 1 shows an overlaid 3D aorta model 100 on a 2D fluoroscopic image for a transcatheter aortic valve implantation (TAVI) procedure. Image (b) of FIG. 1 shows an overlaid left atrium model 110, together with the pulmonary veins 112, 114, 116, and 118, and left atrial appendage 120, on a 2D fluoroscopic image for a transcatheter left atrial fibrillation ablation procedure. FIG. 2 illustrates a workflow for direct 3D to 2D fusion for a TAVI procedure. Image (a) of FIG. 2 shows a pre-operative CT volume 200 with an automatically segmented aortic root mesh 202. Image (b) shows a 2D fluoroscopic image 210 with a contrast injection in the aortic root. Image (c) shows a model fusion result 220 showing the overlaid aortic root model 222 on the 2D fluoroscopic image 210. However, direct fusion of a 3D model with an intra-operative fluoroscopic image, as shown in FIG. 2, is difficult and typically requires manual user interaction and the use of contrast agent in the fluoroscopic image.

Intra-operative C-arm CT (or rotational angiography) is emerging as a new imaging modality for cardiac interventions. A C-arm CT is generated by rotating the C-arm X-ray source/detector during the surgery. The imaging is performed intra-operatively, and therefore provides patient-anatomy at the time of the surgery. Since the 3D C-arm CT and 2D fluoroscopic images are captured on the same machine (i.e., a C-arm image acquisition device), the 3D-to-2D registration is straightforward and accurate (only the cardiac and respiratory motion need to be compensated) using the projection geometry of 2D fluoroscopic images. However, the image quality of C-arm CT volumes is typically not as good as CT or MRI volumes and it is difficult to scan a motion compensated/contrasted C-arm CT in a crowded hybrid operating room. Each rotation of the C-arm takes approximately five seconds and five to six rotations are typically needed to capture enough 2D projection data for each cardiac phase to perform electrocardiogram (ECG) gated reconstruction to remove cardiac motion artifacts. The patient is required to hold his or her breath during the whole procedure of approximately 30 seconds in order to remove respiratory motion, which may be very difficult in sick patients. Furthermore, longer acquisition times incur a larger dose of radiation, which is also an important concern. It is possible that rapid ventricular pacing can be performed to temporarily stop the cardiac motion, but rapid pacing may peel off cardiac plaques into the blood circulation and cause strokes. Injection of contrast medium is often required to highlight the target anatomy in the 3D C-arm CT volume and also to facilitate automatic segmentation of the target anatomy in the 3D C-arm CT volume. However, physicians are typically cautious with the use of contrast agent due to the side effects, such as allergic reaction or renal failure. Intravenous or transcatheter injection of contrast agent requires extra preparation and wiring.

Figure 3:
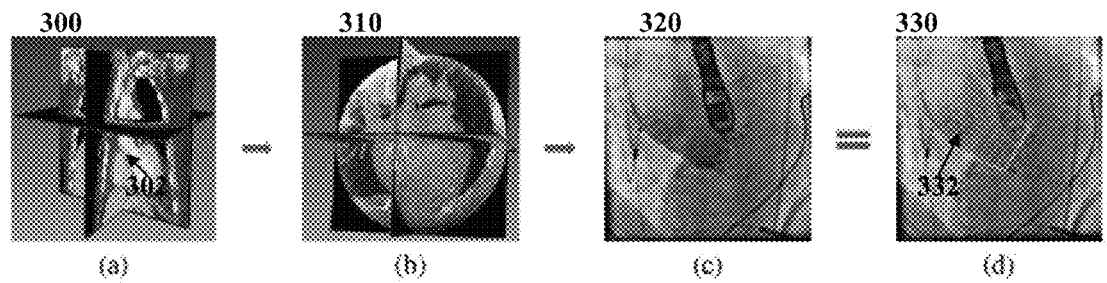
FIG. 3 illustrates fusion of pre-operative CT data to 2D fluoroscopy using non-contrasted C-arm CT as a bridge.

It is much easier to scan a non-ECG-gated (i.e., one sweep of the C-arm) and non-contrasted (i.e., no contrast injection) intra-operative C-arm CT in a crowded hybrid operating room. Although the target anatomy may be hardly visible and difficult to segment automatically in a non-contrasted C-arm CT volume, non-contrasted C-arm CT can act as a bridge to bring a 3D cardiac model extracted from pre-operative images to the 2D fluoroscopic images. FIG. 3 illustrates fusion of pre-operative CT data to 2D fluoroscopy using non-contrasted C-arm CT as a bridge. Image (a) of FIG. 3 shows a pre-operative 3D CT volume 300 with an automatically segmented aortic root mesh 302. Image (b) shows an intra-operative C-arm CT volume 310. Image (a) shows an intra-operative 2D fluoroscopic image 320. Image (d) shows a model fusion result 330 showing the overlaid aortic root model 332 on the 2D fluoroscopic image 320. The model fusion result 330 is obtained by first registering the 3D aortic root mesh 302 to the 3D C-arm CT volume 310, and then overlaying the 3D model registered to the 3D C-arm CT volume onto the 2D fluoroscopic image 320. Overlay of the intra-operative C-arm CT to the fluoroscopy is easy and accurate since the projection geometry of the C-arm system can be directly used.

Figure 4:
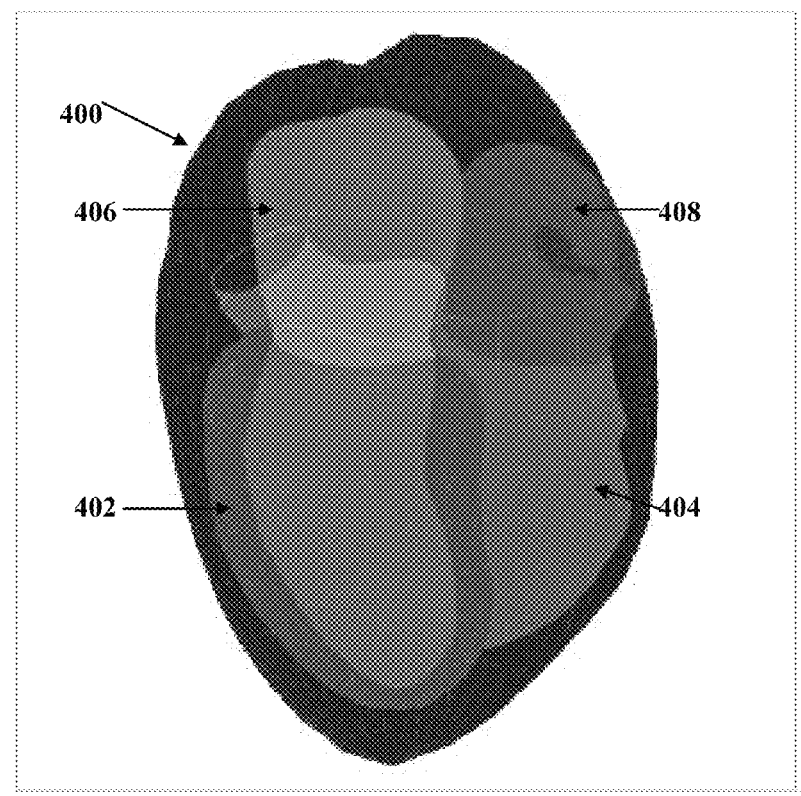
FIG. 4 illustrates a 3D visualization of a pericardium mesh.

Image registration may be used to estimate a deformation field from pre-operative images to C-arm CT for model fusion. However, due to significant differences in image characteristics (e.g., contrasted v. non-contrasted), cross-modality image registration is a difficult problem. If the transformation between the pre-operative and intra-operative images is large, the registration is likely to fail. Furthermore, image registration is very time consuming, especially for non-rigid registration. Embodiments of the present invention utilize model based fusion to align pre-operative and intra-operative C-arm CT. Embodiments of the present invention use an anchor structure that is present and can be reliably segmented in both of the pre-operative images and the non-contrasted intra-operative C-arm CT images. Using the segmented anchor structure, the deformation field can then be estimated and used to warp a model of a target anatomical structure to the C-arm CT. In an advantageous embodiment, the pericardium is used as a reliable anchor structure for fusing pre-operative CT and C-arm CT for cardiac interventions. The pericardium is clearly visible in both CT and C-arm CT images. FIG. 4 illustrates a 3D visualization of a pericardium mesh. As shown in FIG. 4, the pericardium 400 encloses all heart chambers 402, 404, 406, and 408 and is proximal to the epicardium of the chamber free walls. Therefore, the deformation of cardiac structures (e.g., chambers, aorta, and valves) can be inferred well from the pericardium.

Figure 5:
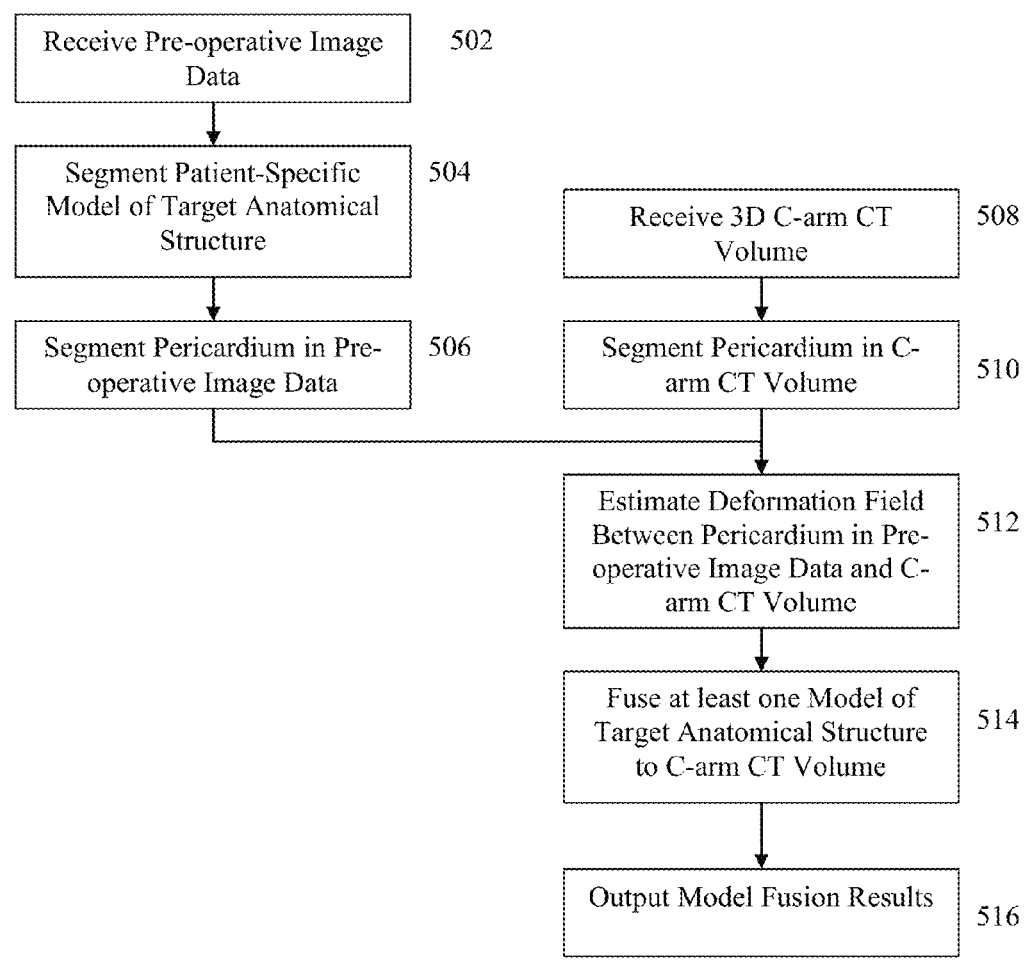
FIG. 5 illustrates a method for model based fusion of pre-operative and intra-operative image data using the pericardium as an anchor structure according to an embodiment of the present invention.

FIG. 5 illustrates a method for model based fusion of pre-operative and intra-operative image data using the pericardium as an anchor structure according to an embodiment of the present invention. In an advantageous embodiment, steps 502-506 of FIG. 5 can be performed in advance of a cardiac intervention procedure and steps 508-514 can be performed at the time of the cardiac intervention procedure. At step 502, pre-operative medical image data of a patient is received. The pre-operative medical image data can be a 3D medical image volume of a patient. In an advantageous embodiment, the pre-operative medical image data is a CT volume of the patient, but the present invention is not limited thereto and other imaging modalities, such as MRI or ultrasound, may be used to acquire the pre-operative medical image data. The pre-operative medical image data may be received directly from an image acquisition device, such as a CT scanner, or may be received by loading previously stored medical image data.

At step 504, a patient-specific model of a target anatomical structure is segmented in the pre-operative medical image data. In an advantageous embodiment, the target anatomical structure can be one or more cardiac structures, such as the chambers (left ventricle, right ventricle, left atrium, and right atrium), the aorta, or the valves (e.g., mitral valve, tricuspid valve, aortic valve, and pulmonary valve). However, the present invention is not limited to any particular target anatomical structures and the method of FIG. 5 may be similarly applied to fuse any other target anatomical structures to intra-operative image data.

The patient-specific model of the target anatomical structure can be segmented in the pre-operative image data using any automatic or semi-automatic segmentation technique. In an advantageous embodiment, Marginal Space Learning (MSL) can be used to automatically segment the target anatomical structure. In particular, MSL-based 3D object detection can be used to detect patient-specific models for the heart chambers and for the heart valves. MSL-based 3D object detection estimates the position, orientation, and scale of the target anatomical structure in the pre-operative 3D medical image data using a series of detectors trained using annotated training data. For example, a method for MSL-based heart chamber segmentation is described in detail in U.S. Pat. No. 7,916,919, issued Mar. 29, 2011, and entitled "System and Method for Segmenting Chambers of a Heart in a Three Dimensional Image", which is incorporated herein by reference. In order to efficiently localize an object using MSL, parameter estimation is performed in a series of marginal spaces with increasing dimensionality. Accordingly, the idea of MSL is not to learn a classifier directly in the full similarity transformation space, but to incrementally learn classifiers in the series of marginal spaces. As the dimensionality increases, the valid space region becomes more restricted by previous marginal space classifiers. The 3D object detection is split into three steps: object position estimation, position-orientation estimation, and position-orientation-scale estimation. A separate classifier is trained based on annotated training data for each of these steps. This object localization stage results in an estimated transformation (position, orientation, and scale) of the object, and a mean shape of the object (i.e., the mean shape of a whole heart surface model in the annotated training images) is aligned with the 3D volume using the estimated transformation. After the object pose estimation, the boundary of the object is refined using a learning based boundary detector.

In a case in which the aorta is the target anatomical structure, a part-based aorta model which splits the aorta into four parts: aortic root, ascending aorta, aortic arch, and descending aorta, can be used to automatically segment the aorta in the pre-operative image data. Such a part-based method for automatically segmenting the aorta is described in more detail in United States Published Patent Application No. 2010/0239148, which is incorporated herein by reference.

At step 506, the pericardium is segmented in the pre-operative image data. It is to be understood that in the embodiment illustrated in FIG. 5, the pericardium is used as an anchor anatomical structure to estimate a deformation field between the pre-operative image data and the intra-operative C-arm CT data. However, the present invention is not limited to the pericardium and other structures, such as the trachea, may be used as the anchor anatomical structure as well. The anchor anatomical structure can be any structure that can be reliably detected in both the pre-operative image data and in the C-arm CT data.

Figure 6:
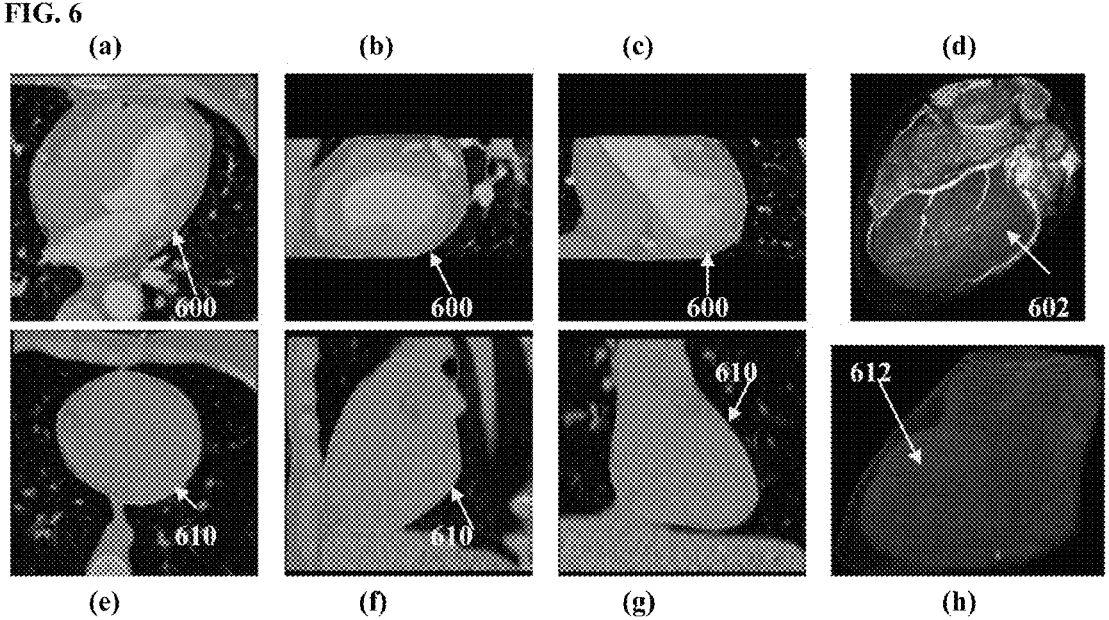
FIG. 6 illustrates exemplary pericardium segmentation results in contrasted and non-contrasted CT volumes.

In an advantageous embodiment of the present invention, the pericardium can be segmented using an efficient and fully automatic method for pericardium segmentation described in United States Published Patent Application No. 2012/0134564, entitled "Method and System for Heart Isolation in Cardiac Computed Tomography Volumes for Patients with Coronary Artery Bypasses," which is incorporated herein by reference. In this pericardium segmentation (heart isolation) method, marginal space learning (MSL) is first utilized to efficiently estimate the position, orientation, and scale of the heart in a CT volume. A learned mean shape is aligned with the estimated pose as an initialization of the heart shape. Learning based boundary detectors are then used to guide boundary evolution. Since the background surrounding the heart is different from chamber to chamber, the whole heart surface is split into four patches with each patch corresponding to a chamber of the heart. A separate boundary detector is trained for each patch. Bright tissues surrounding the heart surface, such as the descending aorta filled with contrast agent and the rib cage, can be completely removed in a post-processing step. A binary pericardium mask is then generated, where voxels inside the heart are set to 1 and all other voxels are set to 0. This method is more robust than previous heart isolation methods and works for both contrasted and non-contrasted CT scans. This method typically takes about 1.5 seconds to process one volume, which is faster than previous methods by at least one order of magnitude. FIG. 6 illustrates exemplary pericardium segmentation results in contrasted and non-contrasted CT volumes. Images (a), (b), and (c) of FIG. 6 show contours of a segmented pericardium mesh 600 in orthogonal cuts of a contrasted CT volume, and image (d) shows a visualization of the segmented heart 602 from the contrasted CT volume. Images (e), (f), and (g) of FIG. 6 show contours of a segmented pericardium mesh 610 in orthogonal cuts of a non-contrasted CT volume, and image (h) shows a visualization of the segmented heart 612 from the non-contrasted CT volume.

Returning to FIG. 5, at step 508, a 3D C-arm CT volume is received. The C-arm CT volume can be an intraoperative CT volume received from a C-arm imaging device at the time of a procedure, such as a cardiac intervention procedure. The C-arm CT volume can be received directly from the C-arm imaging device, or the C-arm CT volume can be received by loading a previously stored C-arm CT volume.

Figure 7:
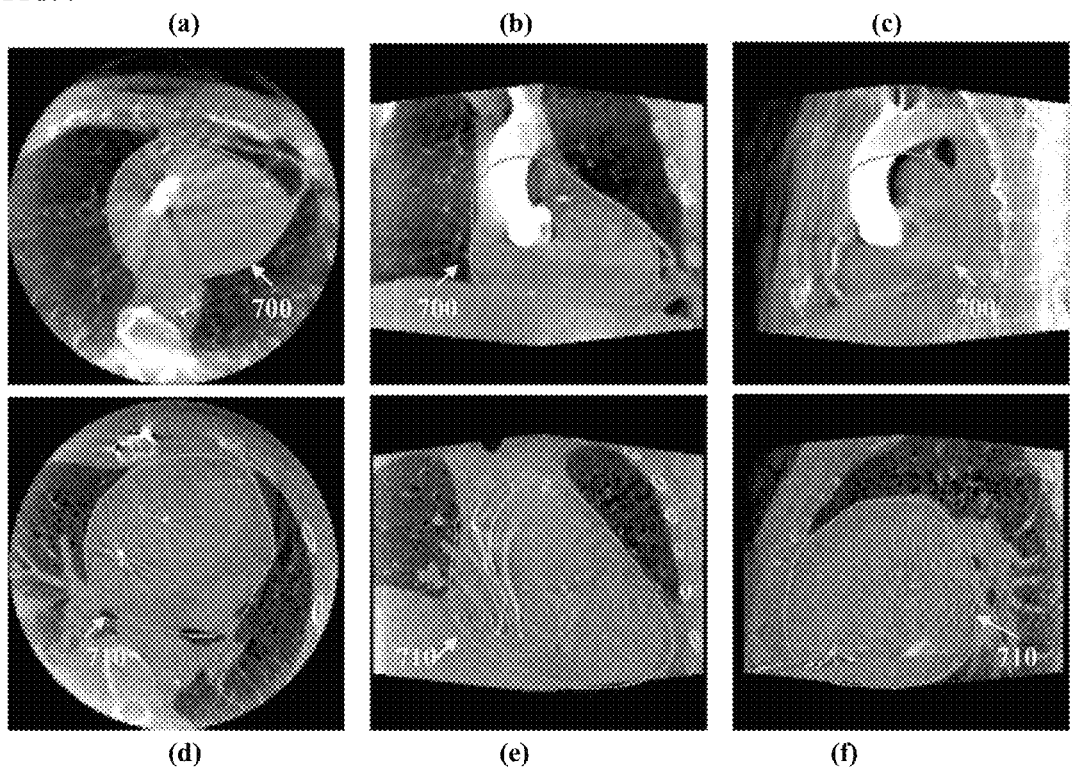
FIG. 7 illustrates exemplary pericardium segmentation results in contrasted and non-contrasted C-arm CT volumes.

At step 510, the pericardium is segmented in the C-arm CT volume. The pericardium can be segmented in the C-arm CT volume using the same pericardium segmentation method described above for segmenting the pericardium in the pre-operative image data. It is to be understood that while the same segmentation method can be used to segments the pericardium in the pre-operative image data and in the intra-operative C-arm CT image, separate learning based detectors (e.g., MSL object detectors and learning based boundary detectors) are trained for each respective imaging modality using annotated training data from the respective imaging modality. FIG. 7 illustrates exemplary pericardium segmentation results in contrasted and non-contrasted C-arm CT volumes. Images (a), (b), and (c) of FIG. 7 show contours of a segmented pericardium mesh 700 in orthogonal cuts of a contrasted C-arm CT volume for transcatheter aortic valve implantation. Images (d), (e), and (f) of FIG. 7 show contours of a segmented pericardium mesh 710 in orthogonal cuts of a non-contrasted C-arm CT volume.

Figure 8:
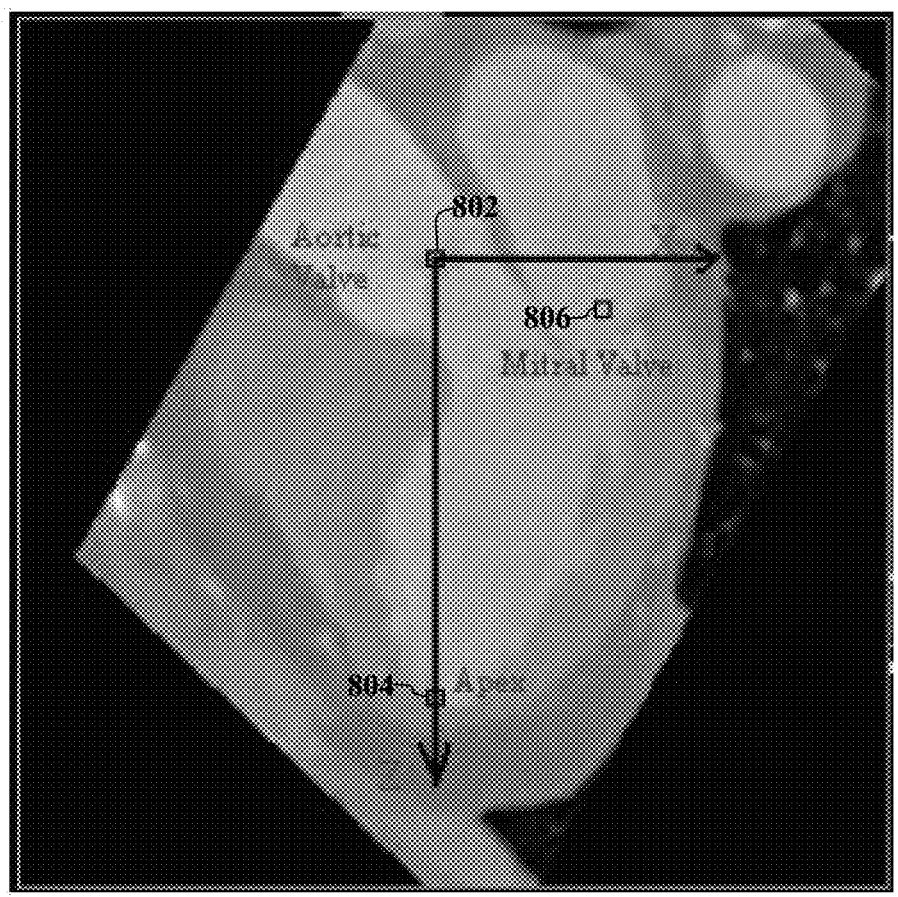
FIG. 8 illustrates a heart coordinate system defined by anatomical landmarks.

As described above, the pericardium is segmented in both the pre-operative image data and the intra-operative C-arm CT volume. The segmented pericardium is used to estimate a deformation field from the pre-operative image data to the C-arm CT volume (step 512 of FIG. 5). Accordingly, the pericardium meshes extracted in the pre-operative image and the C-arm CT need to have the same number of mesh points and corresponding mesh points of the extracted pericardium meshes should have correspondence in anatomy. During training in each imaging modality, a mean shape is calculated from the training set and all training meshes have anatomical correspondence. During the model-driven segmentation procedure, the mean shape is deformed to fit the pericardium boundary on the image under the active shape model framework, therefore the output mesh has built in correspondence. According to an embodiment of the present invention, a sphere mapping based method is used during training for each imaging modality to establish mesh point correspondence in the training data. Suppose there is a sphere together with a set of uniformly sampled points on the sphere. The sphere is aligned according to the intrinsic coordinate system of the heart, which is defined by three landmarks: namely, the aortic valve center, the mitral valve center, and the left ventricle endocardium apex. FIG. 8 illustrates the heart coordinate system defined by the anatomical landmarks. As shown in FIG. 8, the heart center is defined as the aortic valve center 802. The z axis is the direction pointing from the aortic valve center to the left ventricle apex 804. The x axis is defined as the vector perpendicular to the z axis, lying inside the plane formed by three landmarks 802, 804, and 806, and pointing toward the mitral valve center 806. The y axis is the cross product of the z and x axes. After aligning the sphere to the heart coordinate system, each of the uniformly sampled points on the sphere is connected to the sphere center, which results in an intersection point with the pericardium mesh. These intersection points have quite good correspondence in anatomy. A consistently resampled mesh is achieved by triangulating the intersection points into a mesh.

Returning to FIG. 5, at step 512, a deformation field is estimated between the segmented pericardium in the pre-operative image data and the C-arm CT volume. The segmented pericardium meshes from both imaging modalities are used to estimate the deformation field for model fusion. In an advantageous implementation, the well-known thin-plate-spline (TPS) model is used to estimate the deformation field, which minimizes the energy of a thin plate:

$$E = \int\int_{R^2} \left[ \left(\frac{\partial^2 z}{\partial x^2}\right)^2 + 2\left(\frac{\partial^2 z}{\partial x \partial y}\right)^2 + \left(\frac{\partial^2 z}{\partial y^2}\right)^2 \right] dx\,dy. \quad (1)$$

The TPS deformation field is advantageous because the interpolation is smooth with derivatives of any order, the TPS model has no free parameters that need manual tuning, it as closed form a solutions for both warping and parameter estimation, and there is a physical explanation for its energy function. However, the present invention is not limited to the TPS model, and other parametric or non-parametric deformation fields can be used as well.

Figure 9:
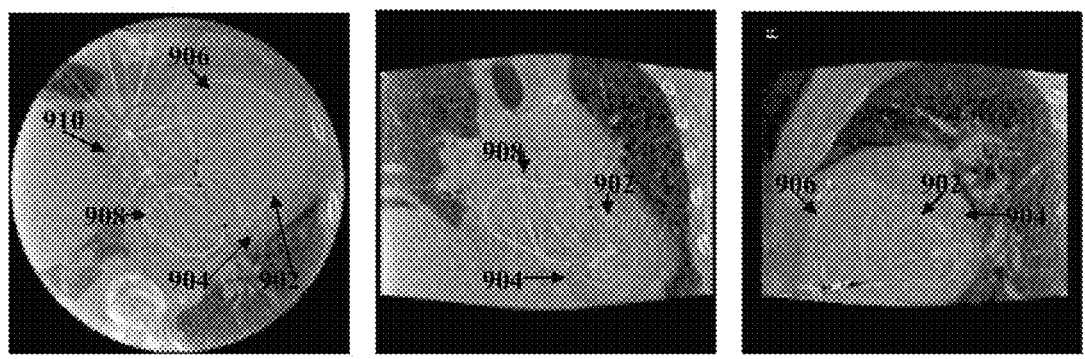
FIG. 9 illustrates fusion of a four-chamber heart model with a non-contrast C-arm CT volume.
Figure 10:
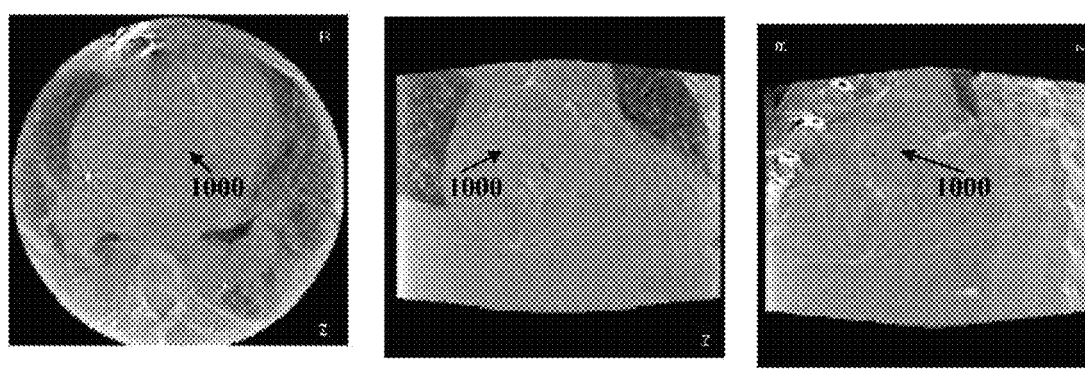
FIG. 10 illustrates fusion of an ascending aorta model with a non-contrasted C-arm CT volume.

At step 514, at least one model of the target anatomical structure is fused to the C-arm CT volume using the deformation field. In one embodiment, the patient-specific model of the target anatomical structure segmented in the pre-operative image data is fused to the C-arm CT volume using the calculated deformation field. For example, the cardiac models (e.g., heart chambers or aorta) segmented in a pre-operative CT volume can be registered to the C-arm CT volume using the deformation field calculated using the segmented pericardium. FIG. 9 illustrates fusion of a four-chamber heart model with a non-contrast C-arm CT volume. As shown in FIG. 9, a four chamber heart model 900 that was extracted from a CT volume is fused with a C-arm CT volume using the deformation field calculated between the segmented pericardium in the CT volume and the segmented pericardium in the C-arm CT volume. The four chamber heart model includes the left ventricle endocardium 902, the left ventricle epicardium 904, the right ventricle 906, the left atrium 908, and the right atrium 910. FIG. 10 illustrates fusion of an ascending aorta model with a non-contrasted C-arm CT volume. As shown in FIG. 10, an ascending aorta model 1000 extracted from a CT volume is fused with a C-arm CT volume using the deformation field calculated between the segmented pericardium in the CT volume and the segmented pericardium in the C-arm CT volume.

In another embodiment, multiple models of the target anatomical structure from different patients can be combined using an intelligent weighted average and fused with the C-arm CT volume. In real clinical practice, not all patients can have a pre-operative CT scan. It is possible to align a target model (i.e., model of a target anatomical structure) from a different patient and a reasonably accurate prediction can be achieved if the target anatomical structure has a similar shape in different patients (e.g., the aorta) and a non-rigid deformation can be used to compensate for some amount of shape variation. Of course, such a predicted model is not as accurate as using a patient-specific pre-operative model for the same patient. However, the target model from the same patient may not be perfect since the pre-operative image data (e.g., CT volume) and C-arm CT are scanned at different times, from different cardiac phases, and with complicated non-rigid deformation between scans. Accordingly, there may still be room for improvement, and according to an embodiment of the present invention, pre-operative models from different patients can be used together with the patient-specific pre-operative model from the same patient to improve the accuracy of model fusion results.

Figure 11:
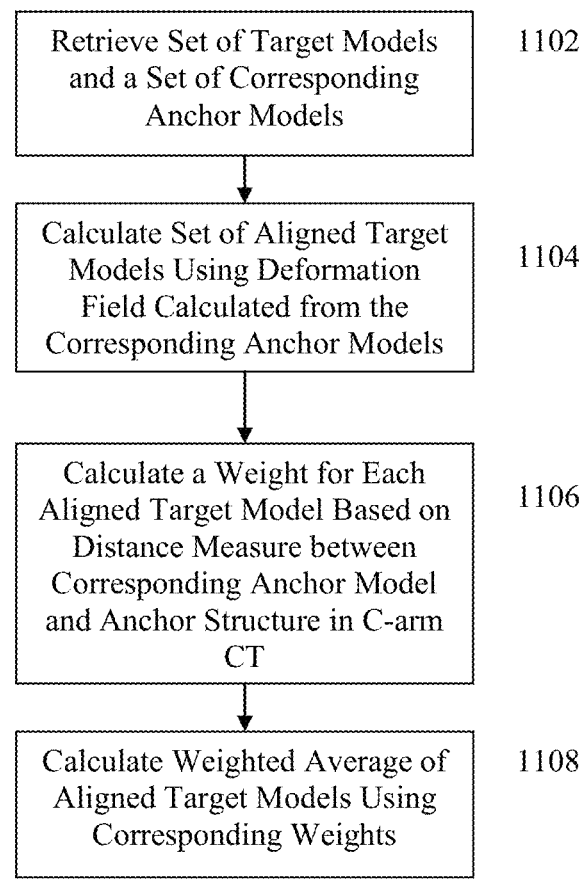
FIG. 11 illustrates an intelligent weighted average method for model fusion according to an embodiment of the present invention.

FIG. 11 illustrates an intelligent weighted average method for model fusion according to an embodiment of the present invention. The method of FIG. 11 can be used to implement step 514 of FIG. 5. As illustrated in FIG. 11, at step 1102, a set of target models and a set of corresponding anchor models are retrieved. The set of target models and the set of corresponding anchor models are stored in a database. For example, suppose there are n patients in a heart model library. For each patient, the target heart model $m_1, m_2, \ldots, m_n$ (e.g., four chamber heart models or aorta) and pericardium $p_1, p_2, \ldots, p_n$ are already segmented, manually corrected if necessary, and stored in the database. Given a current patient with both CT and C-arm CT data available, segmentation is performed to get the target heart model $m_0$ for the current patient (step 504 of FIG. 5) and the pericardium $p_0$ for the current patient (step 506 of FIG. 5) from the pre-operative CT volume. The target heart model $m_0$ and pericardium $p_0$ for the current patient can be segmented from the CT volume and stored in the database at a time prior to the cardiac intervention. The pericardium q from the C-arm CT is also segmented (step 510 of FIG. 5).

At step 1104, set of aligned target models is calculated from the set of target models using deformation fields calculated from the corresponding anchor models. In particular, for each patient i for i=0, 1, . . . , n, a corresponding deformation field is calculated between the corresponding segmented pericardium mesh $p_i$ in the pre-operative image and the segmented pericardium mesh q in the C-arm CT image of the current patient, and the target model $m_i$ is aligned to the C-arm CT image using the corresponding deformation field, resulting in a corresponding aligned target model $a_i$. This results in the set of aligned target models $a_0, a_1, \ldots, a_n$. It is to be understood that i=0 refers to the current patient in the C-arm CT volume.

At step 1106, a weight is calculated for each aligned target model based on a distance measure between the corresponding anchor model and the segmented anchor structure in the C-arm CT volume. The final prediction of the target structure in the C-arm CT volume can be calculated using a weighted average of the aligned target models $a_0, a_1, \ldots, a_n$. In order to determined weights for the aligned target models to generate an accurate fused model a, the weight for each aligned target model $a_i$ is set according to the shape distance between the corresponding pericardium mesh $p_i$ in the pre-operative image and the segmented pericardium mesh q in the C-arm CT volume of the current patient. The underlying idea is that if two patients have a similar shape in the pericardium, they are likely to a similar shape in the target cardiac structure. This assumption is reasonable because the pericardium encloses all cardiac anatomies and is very close to the freewall epicardium of all four chambers. The shape of the pericardium is highly correlated to the inner cardiac anatomies. Therefore if the pericardium shape distance $d(p_i,q)$ is small, a large weight should be assigned to the predicted aligned model $a_i$. The pericardium shape distance can be defined as the average point-to-point distance between the two meshes ($p_i$ and q) after compensating the similarity transform. The distance is further converted to a weight:

$$w_i = 1 - \frac{d_i - d_{min}}{d_{max} - d_{min}}, \quad (2)$$

where $d_{min}$ and $d_{max}$ are the minimum and maximum values of $\{d_0, d_1, \ldots, d_n\}$, respectively. Accordingly, the aligned target model from the pre-operative image of the patient with the most similar pericardium shape to the pericardium shape in the C-arm CT volume of the current patient will have a weight of one and the aligned target model from the pre-operative image of the patient with the pericardium shape most dissimilar to the pericardium shape in the C-arm CT volume of the current patient will have a weight of zero. In cases in which the patient-specific target model $m_0$ of the current patient is included with the set of target models, the corresponding aligned target model $a_0$ of the current patient will likely be assigned the highest weight $w_0=1$, since the pericardium meshes $p_0$ and q are segmented from different images of the same patient.

At step 1108, a weighted average of the aligned target models is calculated using the weights corresponding to the aligned target models. There are various ways to calculate the weighted average. In one possible implementation, the aligned target model of the current patient $a_0$ is not treated differently from the rest of the aligned target models, and the weighted average is calculated as:

$$a = \frac{\sum_{i=0}^{n} w_i a_i}{\sum_{i=0}^{n} w_i}. \quad (3)$$

Here, the denominator is a normalization factor. In another possible implementation, the weighted average can be tuned so that the aligned target model of the current patient $a_0$ is weighted specially relative to the other aligned target models. In this case, the weighted average can be calculated as:

$$a = \frac{\beta a_0 + (1-\beta)\sum_{i=1}^{n} w_i a_i}{\beta + (1-\beta)\sum_{i=1}^{n} w_i}. \quad (4)$$

Here, the aligned target model of the current patient $a_0$ is assigned the highest weight $w_0=1$ and there is an extra parameter $\beta$ to tune the relative weights between the current patient's data and data from all of the different patients. That is $\beta=1$ corresponds to only fusing the current patient's target model with the C-arm CT volume of the current patient, and $\beta=0$ corresponds to only fusing other patient's target models with the C-arm CT volume of the current patient.

Figure 12:
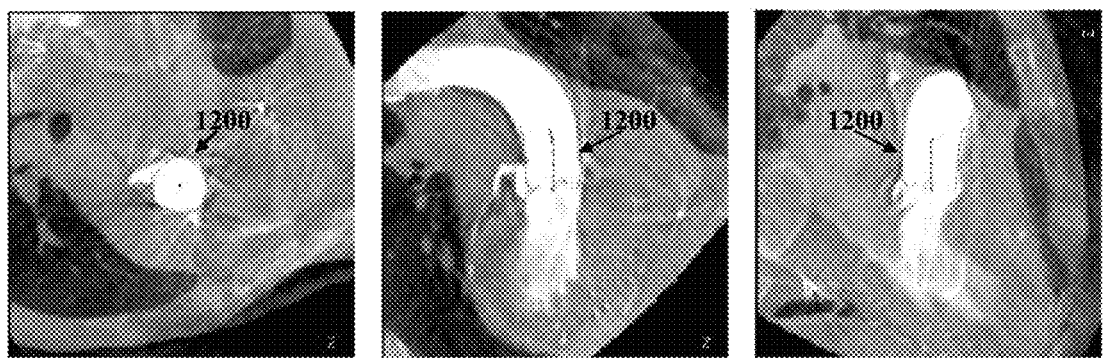
FIG. 12 illustrates fusion of an ascending aorta model with a non-contrasted C-arm CT volume using an intelligent weighed average.

Although the method of FIG. 11 is described above as being used to fuse target cardiac models from pre-operative image data to C-arm CT data based on the pericardium, it is to be understood that the method of FIG. 11 can be similarly applied to fuse any type of target anatomical models extracted in a first imaging modality with a second imaging modality based on any type of anchor anatomical structure. FIG. 12 illustrates fusion of an ascending aorta model with a non-contrasted C-arm CT volume using an intelligent weighed average. As shown in FIG. 12, the fused ascending aorta model 1200 is a weighted average of multiple aorta models extracted from CT volumes and aligned with the C-arm CT volume using respective deformation fields calculated between segmented pericardium meshes in the CT volumes and a segmented pericardium mesh in the C-arm CT volume.

Returning to FIG. 5, at step 516, the model fusion results are output. For example, the 3D C-arm image with the fused model of the target anatomical structure can be displayed on a display of a computer device. Also, the fused model of the target anatomical structure can be overlayed on 2D fluoroscopic images acquired using the C-arm imaging device, for example, for planning or guiding a cardiac intervention procedure.

Figure 13:
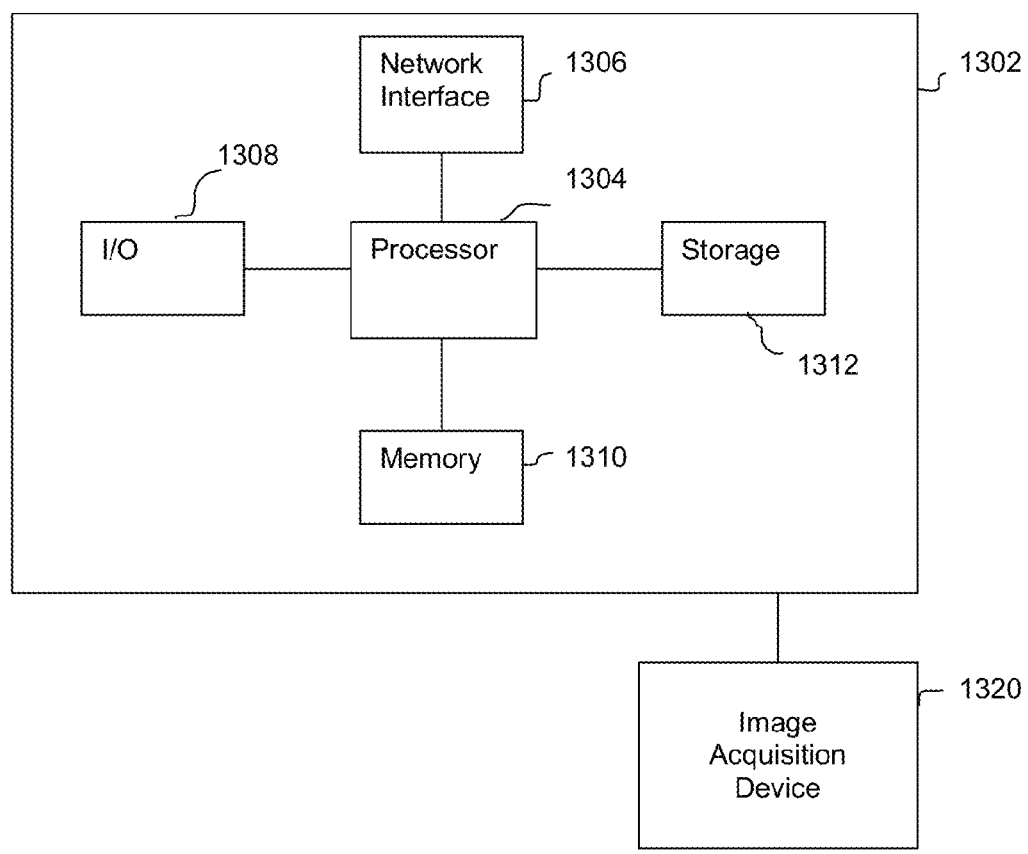
FIG. 13 is a high level block diagram of a computer capable of implementing the present invention.

The above-described methods for model based fusion of pre-operative and intra-operative image data, may be implemented on a computer using well-known computer processors, memory units, storage devices, computer software, and other components. A high level block diagram of such a computer is illustrated in FIG. 13. Computer 1302 contains a processor 1304 which controls the overall operation of the computer 1302 by executing computer program instructions which define such operation. The computer program instructions may be stored in a storage device 1312, or other computer readable medium (e.g., magnetic disk, CD ROM, etc.) and loaded into memory 1310 when execution of the computer program instructions is desired. Thus, the steps of the methods of FIGS. 5 and 11 may be defined by the computer program instructions stored in the memory 1310 and/or storage 1312 and controlled by the processor 1304 executing the computer program instructions. An image acquisition device 1320, such as a CT scanner, can be connected to the computer 1302 to input images to the computer 1302. It is possible to implement the image acquisition device 1320 and the computer 1302 as one device. It is also possible that the image acquisition device 1320 and the computer 1302 communicate wirelessly through a network. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.). One skilled in the art will recognize that an implementation of an actual computer could contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for fusion of a model of a target cardiac structure extracted from a first medical image of a patient acquired using a first imaging modality with a second medical image of the patient acquired using a second imaging modality, comprising:
    segmenting a first pericardium model in the first medical image;
    segmenting a second pericardium model in the second medical image;
    estimating a deformation field between the first pericardium model and the second pericardium model; and
    fusing the model of the target cardiac structure extracted from the first medical image with the second medical image based on the estimated deformation field between the first pericardium model and the second pericardium model, wherein the target cardiac structure is a cardiac structure other than the pericardium and the pericardium is used as anchor structure to fuse the target cardiac structure to the second medical image.

2. The method of claim 1, wherein the first medical image is a pre-operative image and the second medical image is an intra-operative image acquired at the time of a cardiac intervention.

3. The method of claim 1, wherein the first medical image is a computed tomography volume and the second medical image is a C-arm computed tomography volume.

4. The method of claim 1, wherein estimating a deformation field between the first pericardium model and the second pericardium model comprises:
    estimating a deformation field between the first pericardium model and the second pericardium model using a thin plate spline (TPS) model.

5. The method of claim 1, wherein fusing the model of the target cardiac structure extracted from the first medical image with the second medical image based on the estimated deformation field between the first pericardium model and the second pericardium model comprises:
    generating a fused model of the target cardiac structure by transforming the model of the target cardiac structure extracted from the first medical image to the second medical image using the estimated deformation field.

6. The method of claim 1, wherein fusing the model of the target cardiac structure extracted from the first medical image with the second medical image based on the estimated deformation field between the first pericardium model and the second pericardium model comprises:
    generating a patient-specific aligned target model by transforming the model of the target cardiac structure extracted from the first medical image to the second medical image using the estimated deformation field; and
    calculating a respective weight for each of a plurality of aligned target models, the plurality of aligned target models including the patient-specific aligned target model and one or more aligned target models generated from models of the target cardiac structure extracted from medical images of other patients acquired using the first medical imaging modality; and
    generating a fused model of the target cardiac structure in the second medical image as a weighted average of the plurality of aligned target models using the respective weight generated for each of the plurality of aligned target models.

7. The method of claim 6, wherein calculating a respective weight for each of a plurality of aligned target models comprises:
    for each of the aligned target models, calculating a distance measure between a corresponding pericardium model segmented in a corresponding medical image acquired using the first medical imaging modality and the second pericardium model segmented in the second medical image; and
    determining the respective weight for each of the plurality of aligned target models based on the calculated distance measure between the corresponding pericardium model and the second pericardium model.

8. A method for fusing a target anatomical structure from a first medical imaging modality to a second medical imaging modality using a plurality of target models of the target anatomical structure, each extracted from a corresponding first medical image acquired using the first medical imaging modality, and a plurality of anchor models of an anchor anatomical structure, each extracted from a corresponding first medical image, the method comprising:
    aligning each of the plurality of target models to a second medical image of a current patient acquired using the second medical imaging modality using a deformation field calculated between a corresponding one of the plurality of anchor models and a model of the anchor anatomical structure segmented in the second medical image, resulting in a plurality of aligned target models;
    calculating a respective weight for each of the plurality of aligned target models based on a distance measure between the corresponding one of the plurality of anchor models and the model of the anchor anatomical structure segmented in the second medical image; and
    generating a fused model of the target anatomical structure in the second medical image as a weighted average of the plurality of aligned target models using the respective weight calculated for each of the plurality of aligned target models.

9. The method of claim 8, wherein calculating a respective weight for each of the plurality of aligned target models based on a distance measure between the corresponding one of the plurality of anchor models and the model of the anchor anatomical structure segmented in the second medical image comprises:

for each of the plurality of aligned target models, calculating a weight $w_i$ as:

$$w_i = 1 - \frac{d_i - d_{min}}{d_{max} - d_{min}},$$

where $d_i$ is the distance measure between the corresponding on the plurality of anchor models and model of the anchor anatomical structure segmented in the medical image, $d_{min}$ is a minimum distance measure, and $d_{max}$ is a maximum distance measure.

10. The method of claim 8, wherein one of the plurality of target models and a corresponding one of the plurality of anchor models are extracted from a first medical image of the current patient.

11. The method of claim 10, wherein generating a fused model of the target anatomical structure in the second medical image as a weighted average of the plurality of aligned target models using the respective weight calculated for each of the plurality of aligned target models comprises:

generating the fused model $\alpha$ as:

$$\alpha = \frac{\sum_{i=0}^{n} w_i a_i}{\sum_{i=0}^{n} w_i},$$

where $\alpha_0$ is the aligned target model extracted from the first medical image of the current patient, $\alpha_1, \ldots, \alpha_n$ are aligned target models extracted from first medical images of patients other than the current patient, and $w_i$ is the respective weight calculated for each of the aligned target models.

12. The method of claim 10, wherein generating a fused model of the target anatomical structure in the second medical image as a weighted average of the plurality of aligned target models using the respective weight calculated for each of the plurality of aligned target models comprises:

generating the fused model $\alpha$ as:

$$\alpha = \frac{\beta a_0 + (1-\beta)\sum_{i=1}^{n} w_i a_i}{\beta + (1-\beta)\sum_{i=1}^{n} w_i},$$

where $\alpha_0$ is the aligned target model extracted from the first medical image of the current patient, $\alpha_1, \ldots, \alpha_n$ are aligned target models extracted from first medical images of patients other than the current patient, $w_i$ is the respective weight calculated for each of the aligned target models, and $\beta$ is a parameter to tune the relative weighting between the aligned target model extracted from the first medical image of the current patient and the aligned target models extracted from first medical images of patients other than the current patient.

13. The method of claim 8, wherein the each first medical image is a computed tomography image, the second medical image is a C-arm computed tomography image, the anchor anatomical structure is the pericardium, and the target anatomical structure is at least one of a heart chamber or an aorta.

14. An apparatus for fusion of a model of a target cardiac structure extracted from a first medical image of a patient acquired using a first imaging modality with a second medical image of the patient acquired using a second imaging modality, comprising:

means for segmenting a first pericardium model in the first medical image;

means for segmenting a second pericardium model in the second medical image;

means for estimating a deformation field between the first pericardium model and the second pericardium model; and means for fusing the model of the target cardiac structure extracted from the first medical image with the second medical image based on the estimated deformation field between the first pericardium model and the second pericardium model, wherein the target cardiac structure is a cardiac structure other than the pericardium and the pericardium is used as anchor structure to fuse the target cardiac structure to the second medical image.

15. The method of claim 14, wherein the first medical image is a computed tomography volume and the second medical image is a C-arm computed tomography volume.

16. The apparatus of claim 14, wherein the means for fusing the model of the target cardiac structure extracted from the first medical image with the second medical image based on the estimated deformation field between the first pericardium model and the second pericardium model comprises:

means for generating a fused model of the target cardiac structure by transforming the model of the target cardiac structure extracted from the first medical image to the second medical image using the estimated deformation field.

17. The apparatus of claim 14, wherein the means for fusing the model of the target cardiac structure extracted from the first medical image with the second medical image based on the estimated deformation field between the first pericardium model and the second pericardium model comprises:

means for generating a patient-specific aligned target model by transforming the model of the target cardiac structure extracted from the first medical image to the second medical image using the estimated deformation field; and means for calculating a respective weight for each of a plurality of aligned target models, the plurality of aligned target models including the patient-specific aligned target model and one or more aligned target models generated from models of the target cardiac structure extracted from medical images of other patients acquired using the first medical imaging modality; and means for generating a fused model of the target cardiac structure in the second medical image as a weighted average of the plurality of aligned target models using the respective weight generated for each of the plurality of aligned target models.

18. The apparatus of claim 17, wherein the means for calculating a respective weight for each of a plurality of aligned target models comprises:

means for determining the respective weight for each of the plurality of aligned target models based on a distance measure between a corresponding pericardium model segmented in a corresponding medical image acquired using the first medical imaging modality and the second pericardium model segmented in the second medical image.

19. An apparatus for fusing a target anatomical structure from a first medical imaging modality to a second medical imaging modality using a plurality of target models of the target anatomical structure, each extracted from a corresponding first medical image acquired using the first medical imaging modality, and a plurality of anchor models of an anchor anatomical structure, each extracted from a corresponding first medical image, comprising:

means for aligning each of the plurality of target models to a second medical image of a current patient acquired using the second medical imaging modality using a deformation field calculated between a corresponding one of the plurality of anchor models and a model of the anchor anatomical structure segmented in the second medical image, resulting in a plurality of aligned target models;

means for calculating a respective weight for each of the plurality of aligned target models based on a distance measure between the corresponding one of the plurality of anchor models and the model of the anchor anatomical structure segmented in the second medical image; and means for generating a fused model of the target anatomical structure in the second medical image as a weighted average of the plurality of aligned target models using the respective weight calculated for each of the plurality of aligned target models.

20. The apparatus of claim 19, wherein one of the plurality of target models and a corresponding one of the plurality of anchor models are extracted from a first medical image of the current patient.

21. The apparatus of claim 19, wherein the each first medical image is a computed tomography image, the second medical image is a C-arm computed tomography image, the anchor anatomical structure is the pericardium, and the target anatomical structure is at least one of a heart chamber or an aorta.

22. A non-transitory computer readable medium storing computer program instructions for fusion of a model of a target cardiac structure extracted from a first medical image of a patient acquired using a first imaging modality with a second medical image of the patient acquired using a second imaging modality, the computer program instructions when executed on a processor causing the processor to perform operations comprising:

segmenting a first pericardium model in the first medical image;

segmenting a second pericardium model in the second medical image;

estimating a deformation field between the first pericardium model and the second pericardium model; and fusing the model of the target cardiac structure extracted from the first medical image with the second medical image based on the estimated deformation field between the first pericardium model and the second pericardium model, wherein the target cardiac structure is a cardiac structure other than the pericardium and the pericardium is used as anchor structure to fuse the target cardiac structure to the second medical image.

23. The non-transitory computer readable medium of claim 22, wherein the first medical image is a computed tomography volume and the second medical image is a C-arm computed tomography volume.

24. The non-transitory computer readable medium of claim 22, wherein fusing the model of the target cardiac structure extracted from the first medical image with the second medical image based on the estimated deformation field between the first pericardium model and the second pericardium model comprises:

generating a fused model of the target cardiac structure by transforming the model of the target cardiac structure extracted from the first medical image to the second medical image using the estimated deformation field.

25. The non-transitory computer readable medium of claim 22, wherein fusing the model of the target cardiac structure extracted from the first medical image with the second medical image based on the estimated deformation field between the first pericardium model and the second pericardium model comprises:

generating a patient-specific aligned target model by transforming the model of the target cardiac structure extracted from the first medical image to the second medical image using the estimated deformation field; and calculating a respective weight for each of a plurality of aligned target models, the plurality of aligned target models including the patient-specific aligned target model and one or more aligned target models generated from models of the target cardiac structure extracted from medical images of other patients acquired using the first medical imaging modality; and generating a fused model of the target cardiac structure in the second medical image as a weighted average of the plurality of aligned target models using the respective weight generated for each of the plurality of aligned target models.

26. The non-transitory computer readable medium of claim 25, wherein calculating a respective weight for each of a plurality of aligned target models comprises:

for each of the aligned target models, calculating a distance measure between a corresponding pericardium model segmented in a corresponding medical image acquired using the first medical imaging modality and the second pericardium model segmented in the second medical image; and determining the respective weight for each of the plurality of aligned target models based on the calculated distance measure between the corresponding pericardium model and the second pericardium model.

27. A non-transitory computer readable medium storing computer program instructions for fusing a target anatomical structure from a first medical imaging modality to a second medical imaging modality using a plurality of target models of the target anatomical structure, each extracted from a corresponding first medical image acquired using the first medical imaging modality, and a plurality of anchor models of an anchor anatomical structure, each extracted from a corresponding first medical image, the computer program instructions when executed on a processor causing the processor to perform operations comprising:

aligning each of the plurality of target models to a second medical image of a current patient acquired using the second medical imaging modality using a deformation field calculated between a corresponding one of the plurality of anchor models and a model of the anchor anatomical structure segmented in the second medical image, resulting in a plurality of aligned target models;

calculating a respective weight for each of the plurality of aligned target models based on a distance measure between the corresponding one of the plurality of anchor models and the model of the anchor anatomical structure segmented in the second medical image; and generating a fused model of the target anatomical structure in the second medical image as a weighted average of the plurality of aligned target models using the respective weight calculated for each of the plurality of aligned target models.

28. The non-transitory computer readable medium of claim 27, wherein calculating a respective weight for each of the plurality of aligned target models based on a distance measure between the corresponding one of the plurality of anchor models and the model of the anchor anatomical structure segmented in the second medical image comprises:

for each of the plurality of aligned target models, calculating a weight $w_i$ as:

$$w_i = 1 - \frac{d_i - d_{min}}{d_{max} - d_{min}},$$

where $d_i$ is the distance measure between the corresponding on the plurality of anchor models and model of the anchor anatomical structure segmented in the medical image, $d_{min}$ is a minimum distance measure, and $d_{max}$ is a maximum distance measure.

29. The non-transitory computer readable medium of claim 27, wherein one of the plurality of target models and a corresponding one of the plurality of anchor models are extracted from a first medical image of the current patient.

30. The non-transitory computer readable medium of claim 29, wherein generating a fused model of the target anatomical structure in the second medical image as a weighted average of the plurality of aligned target models using the respective weight calculated for each of the plurality of aligned target models comprises:

generating the fused model $\alpha$ as:

$$a = \frac{\sum_{i=0}^{n} w_i a_i}{\sum_{i=0}^{n} w_i},$$

where $\alpha_0$ is the aligned target model extracted from the first medical image of the current patient, $\alpha_1, \ldots, \alpha_n$ are aligned target models extracted from first medical images of patients other than the current patient, and $w_i$ is the respective weight calculated for each of the aligned target models.

31. The non-transitory computer readable medium of claim 29, wherein generating a fused model of the target anatomical structure in the second medical image as a weighted average of the plurality of aligned target models using the respective weight calculated for each of the plurality of aligned target models comprises:

generating the fused model $\alpha$ as:

$$a = \frac{\beta a_0 + (1-\beta)\sum_{i=1}^{n} w_i a_i}{\beta + (1-\beta)\sum_{i=1}^{n} w_i},$$

where $\alpha_0$ is the aligned target model extracted from the first medical image of the current patient, $\alpha_1, \ldots, \alpha_n$ are aligned target models extracted from first medical images of patients other than the current patient, $w_i$ is the respective weight calculated for each of the aligned target models, and $\beta$ is a parameter to tune the relative weighting between the aligned target model extracted from the first medical image of the current patient and the aligned target models extracted from first medical images of patients other than the current patient.

32. The non-transitory computer readable medium of claim 27, wherein the each first medical image is a computed tomography image, the second medical image is a C-arm computed tomography image, the anchor anatomical structure is the pericardium, and the target anatomical structure is at least one of a heart chamber or an aorta.

* * * * *